United States Patent
Tanaka et al.

(10) Patent No.: US 10,617,750 B2
(45) Date of Patent: *Apr. 14, 2020

(54) PARTNER OF SLD FIVE 1 (PSF1)-DERIVED PEPTIDE

(71) Applicant: Vasculead Inc., Osaka-shi, Osaka (JP)

(72) Inventors: Hidekazu Tanaka, Toyonaka (JP); Motofumi Iguchi, Toyonaka (JP); Mari Yokoyama, Toyonaka (JP)

(73) Assignee: Vasculead Inc., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/891,238

(22) Filed: Feb. 7, 2018

(65) Prior Publication Data

US 2018/0169203 A1 Jun. 21, 2018

Related U.S. Application Data

(60) Division of application No. 15/413,343, filed on Jan. 23, 2017, now Pat. No. 9,919,039, which is a continuation of application No. 14/424,981, filed as application No. PCT/JP2013/073084 on Aug. 29, 2013, now Pat. No. 9,683,016.

(30) Foreign Application Priority Data

Aug. 31, 2012 (JP) ................ 2012-191050

(51) Int. Cl.
*A61K 39/00* (2006.01)
*A61K 38/00* (2006.01)
*A61K 48/00* (2006.01)
*C07K 7/06* (2006.01)
*C07K 7/08* (2006.01)
*C07K 14/47* (2006.01)

(52) U.S. Cl.
CPC .......... *A61K 39/0011* (2013.01); *A61K 38/00* (2013.01); *C07K 7/06* (2013.01); *C07K 7/08* (2013.01); *C07K 14/4702* (2013.01); *A61K 48/00* (2013.01); *A61K 2039/53* (2013.01); *A61K 2039/572* (2013.01)

(58) Field of Classification Search
CPC .......... A61K 2039/53; A61K 2039/572; A61K 39/0011; A61K 39/00; A61K 48/00; A61K 38/00; C07K 14/4702; C07K 7/06; C07K 7/08
USPC ......... 514/21.7, 19.3, 21.5, 19.8, 21.6, 21.8; 530/327, 328
See application file for complete search history.

(56) References Cited

U.S. PATENT DOCUMENTS

2009/0053714 A1* 2/2009 Bell .................... G01N 33/574
435/6.19

FOREIGN PATENT DOCUMENTS

| WO | 2003/033675 A2 | 4/2003 |
| WO | 2007/119515 A1 | 10/2007 |
| WO | 2008/102557 A1 | 8/2008 |

OTHER PUBLICATIONS

UniProt J9NYU2 from http://www.uniprot.org/uniprot/J9NYU2?sort=score, pp. 1-5. Integrated into UniProtKB/TrEMBL Oct. 31, 2012.*
UniProt K7EEU3 from http://www.uniprot.org/uniprot/K7EEU3?sort=score, pp. 1-5. Integrated into UniProtKB/TrEMBL Jan. 9, 2013.*
Izumi Nakahara et al., "Up-regulation of PSF1 promotes the growth of breast cancer cells" The 32nd Annual Meeting of the Molecular Biology Society of Japan, Dec. 9, 2009-Dec. 12, 2009.

* cited by examiner

*Primary Examiner* — Julie Ha
(74) *Attorney, Agent, or Firm* — McBee Moore & Vanik IP, LLC

(57) ABSTRACT

A Partner of Sld Five 1 (PSF1)-derived peptide that can induce a Cytotoxic T-Cell (CTL) response useful for a specific immunotherapy for cancer patients and a pharmaceutical composition for treating or preventing cancer, which contains the peptide according to the present invention are described.

6 Claims, 4 Drawing Sheets

Specification includes a Sequence Listing.

Figure 2
Fig. 2A
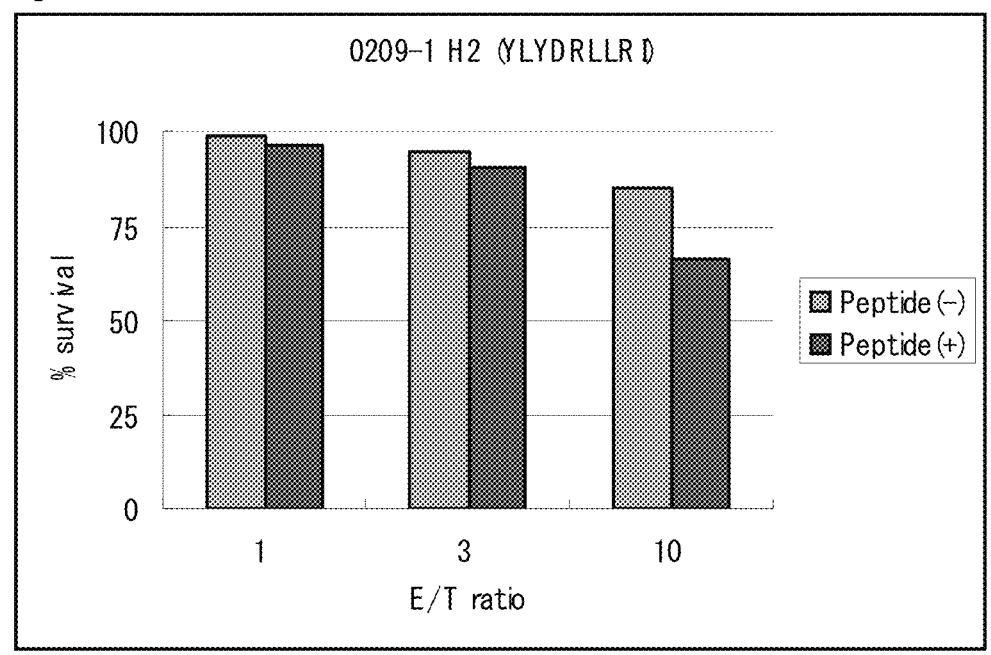
Fig. 2B
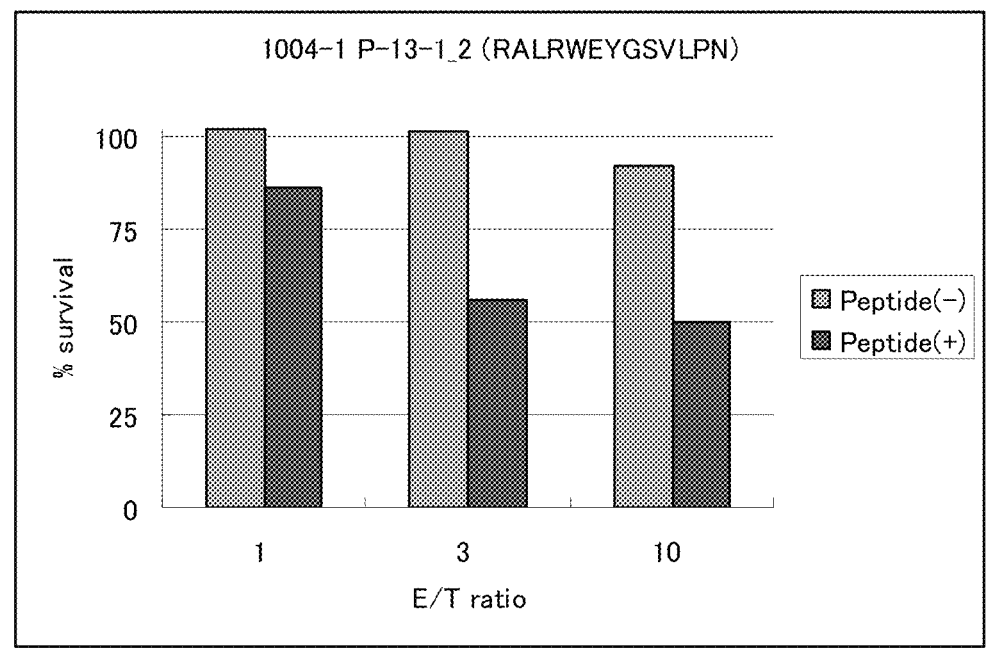

Fig. 3

1   MFCEKQMELIRELHRAFEGQLFAFNEDGLKQVLEEMKALYEQNQSDVNEAKSGGRSDLIP   60

61  TIKFRECSLLRNRRCTVAYLYDRLLRIRALRMEYGSVLPNALRFHMAAEDMEWFNNYKRS   120

121 LATYNRSLGGDEGLDITQDMKPPRSLYIEVRCLKDYGEFEVDDSTSVLLKYNSQHFLPRW   180

181 KCEQLIPQGVLSHTLS   196

SEQUENCE LISTING

```
<160> NUMBER OF SEQ ID NOS: 9

<210> SEQ ID NO 1
<211> LENGTH: 196
<212> TYPE: PRT
<213> ORGANISM: Homo sapiens

<400> SEQUENCE: 1

Met Phe Cys Glu Lys Ala Met Glu Leu Ile Arg Glu Leu His Arg Ala
1               5                   10                  15

Pro Glu Gly Gln Leu Pro Ala Phe Asn Glu Asp Gly Leu Arg Gln Val
            20                  25                  30

Leu Glu Glu Met Lys Ala Leu Tyr Glu Gln Asn Gln Ser Asp Val Asn
        35                  40                  45

Glu Ala Lys Ser Gly Gly Arg Ser Asp Leu Ile Pro Thr Ile Lys Phe
    50                  55                  60

Arg His Cys Ser Leu Leu Arg Asn Arg Arg Cys Thr Val Ala Tyr Leu
65                  70                  75                  80

Tyr Asp Arg Leu Leu Arg Ile Arg Ala Leu Arg Trp Glu Tyr Gly Ser
                85                  90                  95

Val Leu Pro Asn Ala Leu Arg Phe His Met Ala Ala Glu Glu Met Glu
            100                 105                 110

Trp Phe Asn Asn Tyr Lys Arg Ser Leu Ala Thr Tyr Met Arg Ser Leu
        115                 120                 125

Gly Gly Asp Glu Gly Leu Asp Ile Thr Gln Asp Met Lys Pro Pro Lys
    130                 135                 140

Ser Leu Tyr Ile Glu Val Arg Cys Leu Lys Asp Tyr Gly Glu Phe Glu
145                 150                 155                 160

Val Asp Asp Gly Thr Ser Val Leu Leu Lys Lys Asn Ser Gln His Phe
                165                 170                 175

Leu Pro Arg Trp Lys Cys Glu Gln Leu Ile Arg Gln Gly Val Leu Glu
            180                 185                 190

His Ile Leu Ser
        195

<210> SEQ ID NO 2
<211> LENGTH: 595
<212> TYPE: DNA
<213> ORGANISM: Homo sapiens

<400> SEQUENCE: 2
atgttctgcg aaaaagccat ggaactgatc cgcgagctgc atcgcgcgcc cgaagggcaa      60
ctgcctgcct tcaacgagga tggactcaga caagttctgg aggagatgaa agctttgtat     120
gaacaaaacc agtctgatgt gaatgaagca aagtcaggtg gacgaagtga tttgatacca     180
```

-continued

```
actatcaaat ttcgacactg ttctctgtta agaaatcgac gctgcactgt agcatacctg    240
tatgaccgct tgcttcggat cagagcactc agatgggaat atggtagcgt cttgccaaat    300
gcattacgat ttcacatggc tgctgaagaa atggagtggt ttaataatta taaaagatct    360
cttgctactt atatgaggtc actgggagga gatgaaggtt tggacattac acaggatatg    420
aaaccaccaa aaagcctata tattgaagtc cggtgtctaa aagactatgg agaatttgaa    480
gttgatgatg gcacttcagt cctattaaaa aaaaatagcc agcactttt acctcgatgg     540 aaatgtgagc agctgatcag acaaggagtc ctggagcaca tcctgtcatg accat         595
```

<210> SEQ ID NO 3
<211> LENGTH: 9
<212> TYPE: PRT
<213> ORGANISM: Artificial Sequence
<220> FEATURE:
<223> OTHER INFORMATION: peptide

<400> SEQUENCE: 3

Tyr Leu Tyr Asp Arg Leu Leu Arg Ile
1               5

<210> SEQ ID NO 4
<211> LENGTH: 13
<212> TYPE: PRT
<213> ORGANISM: Artificial Sequence
<220> FEATURE:
<223> OTHER INFORMATION: peptide

<400> SEQUENCE: 4

Arg Ala Leu Arg Trp Glu Tyr Gly Ser Val Leu Pro Asn
1               5                   10

<210> SEQ ID NO 5
<211> LENGTH: 8
<212> TYPE: PRT
<213> ORGANISM: Artificial Sequence
<220> FEATURE:
<223> OTHER INFORMATION: peptide

<400> SEQUENCE: 5

Ala Leu Arg Trp Glu Tyr Gly Ser
1               5

<210> SEQ ID NO 6
<211> LENGTH: 10
<212> TYPE: PRT
<213> ORGANISM: Artificial Sequence
<220> FEATURE:
<223> OTHER INFORMATION: peptide

<400> SEQUENCE: 6

Ala Tyr Leu Tyr Asp Arg Leu Leu Arg Ile
1               5                   10

<210> SEQ ID NO 7
<211> LENGTH: 10
<212> TYPE: PRT
<213> ORGANISM: Artificial Sequence
<220> FEATURE:
<223> OTHER INFORMATION: peptide

<400> SEQUENCE: 7

Tyr Leu Tyr Asp Arg Leu Leu Arg Ile Arg
1               5                   10

```
<210> SEQ ID NO 8
<211> LENGTH: 10
<212> TYPE: PRT
<213> ORGANISM: Artificial Sequence
<220> FEATURE:
<223> OTHER INFORMATION: peptide

<400> SEQUENCE: 8

Ala Leu Arg Trp Glu Tyr Gly Ser Val Leu
1               5                   10

<210> SEQ ID NO 9
<211> LENGTH: 10
<212> TYPE: PRT
<213> ORGANISM: Artificial Sequence
<220> FEATURE:
<223> OTHER INFORMATION: peptide

<400> SEQUENCE: 9

Arg Ala Leu Arg Trp Glu Tyr Gly Ser Val
1               5                   10
```

PARTNER OF SLD FIVE 1 (PSF1)-DERIVED PEPTIDE

CROSS-REFERENCE TO RELATED APPLICATIONS

This application is a divisional application of, and claims the benefit of, co-pending U.S. patent application Ser. No. 15/413,343, filed on Jan. 23, 2017, which is a continuation of Ser. No. 14/424,981, filed on Feb. 27, 2015, which is a national phase application under 35 U.S.C. § 371 of International Application No. PCT/JP2013/073084, filed on Aug. 29, 2013, which claims priority under 35 U.S.C. § 119 to Japanese Patent Application No. 2012-191050, filed on Aug. 31, 2012, the contents of which are hereby incorporated by reference in their entirety for all purposes.

TECHNICAL FIELD

The present invention relates to PSF1-derived peptides which are useful for the specific immunotherapy for Human Leucocyte Antigen-A02 (HLA-A02) positive cancer patients.

BACKGROUND OF THE DISCLOSURE

PSF1 forms tetramer, go-ichi-ni-san (GINS) complex, with SLD5, PSF2 and PSF3 of constitutive protein, which binds to MCM (mini-chromosome maintenance complex) and cell division cycle 45 (cdc45). That is known to be associated with initiation of DNA replication and elongation (non-patent reference 1: Structure of the human GINS complex and its assembly and functional interface in replication initiation. Kamada et al. Nat. Struct. Mol. Biol. 2007; 14:388-396 and non-patent reference 2: The human GINS complex associates with cdc45 and MCM and is essential for DNA replication. Aparicio et al. Nucleic Acid Res. 2009; 37:2087-2095).

With respect to the relation with cancer, the expression of PSF1 is considered to increase in human breast cancer cell. It is also reported that the reduction of the expression of PSF1 had caused the suppression of proliferation significantly. Furthermore, it is reported that overall survival rate among breast cancer patients, of which the PSF1 expression level is low in its cancer tissue, is significantly higher, compared to the patients, of which the level is high (non-patent reference 3: Up-regulation of psf1 promotes the growth of breast cancer cells. Izumi et al. Genes to Cells 2010; 15:1025-1024).

Expression of PSF1 has been documented in the cancer tissue derived from malignant melanoma, lung cancer and esophagus cancer (Non-patent reference 4: Comprehensive expression profiling of tumor cell lines identifies molecular signatures of melanoma progression. Ryu B. et al. ProsOne 2007; 7:e594, Non-patent reference 5: PSF1, a DNA replication factor expressed widely in stem and progenitor cells, drives tumorigenic and metastatic properties. Nagahama Y. et al. Cancer Res. 2010; 70:1215-24, and Patent document 1: International Publication Gazette WO2003/42661). The relation between PSF1 and the cancer stem cell is also known in non-patent reference 5.

SUMMARY OF THE INVENTION

An object of the present invention is to provide a peptide which is useful for the specific immunotherapy for cancer patients. Our inventors found PSF1-derived peptides, which is associated with the extracellular domain of HLA-A02 molecule on human breast cancer cell strain. And they confirmed that these peptides had induced a peptide specific CTL (cellular cytotoxicity T-cell) and achieved the present invention.

In accordance with one aspect of the present invention, there is provided a peptide having CTL inducibility, where the peptide is derived from an amino acid sequence of SEQ ID NO: 1. In this embodiment, the peptide includes the continuous 8-14 base within 70-110 of SEQ ID NO.: 1.

In accordance with a second aspect of the present invention, there is provided a peptide having CTL inducibility that includes an amino acid sequence of SEQ ID NO.: 3, 4, or 5.

In accordance with a third aspect of the present invention, there is provided a peptide consisting of an amino acid sequence of SEQ ID NO.: 3, 4, or 5. In this embodiment, 1, 2, or several amino acids are substituted, deleted, or added in the amino acid sequence of SEQ ID NO.: 3, 4, or 5.

According to the embodiments of the present invention, PSF1-derived peptides having inducibility of CTL, which can kill tumor cells in HLA-A02$^+$ cancer patients, are provided. Accordingly, the specific immunotherapy for HLA-A02$^+$ cancer patients becomes possible.

BRIEF DESCRIPTION OF THE DRAWINGS

The present disclosure is described in conjunction with the appended figures:

FIG. 2A shows cellular cytotoxicity by a peptide specific CTL line. Peptide-pulsed cells (peptide+) or peptide-non-pulsed cells (peptide-) obtained from CTL specific to peptide YLYDRLLRI (SEQ ID NO.: 3) (E; effector cell) and T2 cells (T; target cell) were cocultured at an E:T cell ratio of 1:1, 3:1, and 10:1. On the next day, the survival rate of target cells was obtained. Then, it was found that the survival rate of target cells pulsed with peptides decreased to a degree greater than target cells not pulsed with peptides. In addition, since the survival rate decreased in accordance with the ratio of cocultured cells, cellular cytotoxicity by peptide specific CTL was demonstrated.

FIG. 2B shows cellular cytotoxicity by a peptide specific CTL line. Peptide-pulsed cells (peptide+) or peptide-non-pulsed cells (peptide-) obtained from CTL specific to peptide RALRWEYGSVLPN (SEQ ID NO.: 4) (E; effector cell) and T2 cells (T; target cell) were cocultured at an E:T cell ratio of 1:1, 3:1, and 10:1. On the next day, the survival rate of target cells was obtained. Then, it was found that the survival rate of target cells pulsed with peptides decreased to a degree greater than target cells not pulsed with peptides. In addition, since the survival rate decreased in accordance with the ratio of cocultured cells, cellular cytotoxicity by peptide specific CTL was demonstrated.

FIG. 3 shows the positions of YLYDRLLRI (SEQ ID NO.: 3), RALRWEYGSVLPN (SEQ ID NO.: 4), and ALRWEYGSV (SEQ ID NO.: 5) in an amino acid sequence of PSF1 (SEQ ID NO.: 1). All the three peptides are located in the region from 79 to 100 of PSF1.

DETAILED DESCRIPTION OF THE PREFERRED EMBODIMENT

Figure 1:
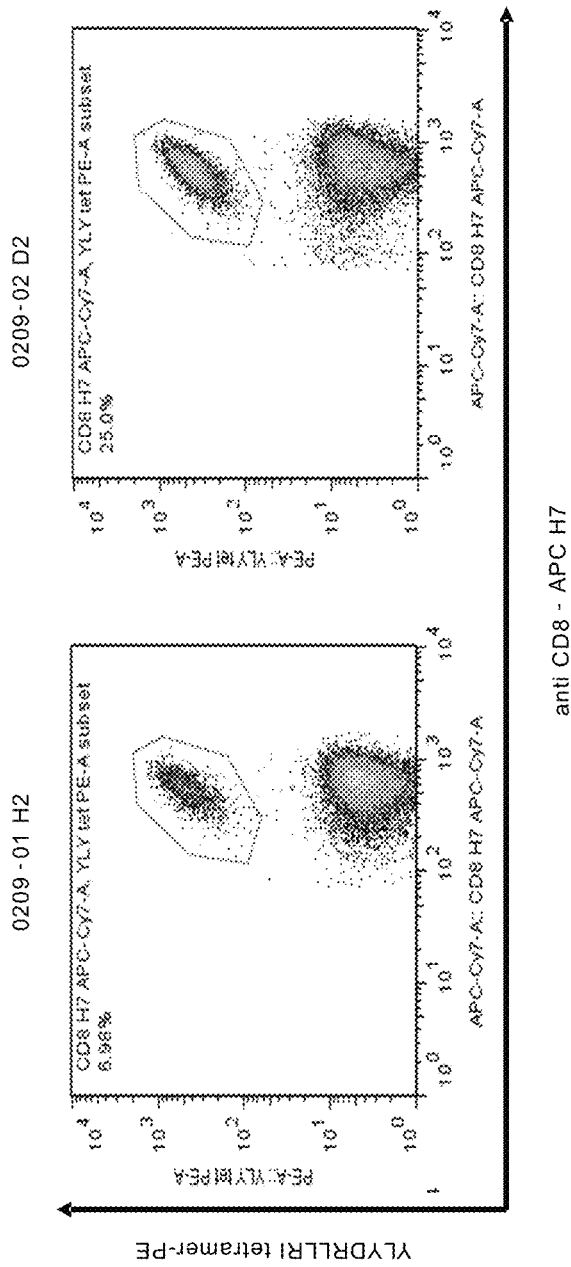
FIG. 1 shows a result of detection of a peptide specific CTL by tetramer staining. CTL cells obtained by incubation were subjected to double staining with PE-labeled tetramer and APC-H7-labeled anti-CD8 antibodies so that the fluorescent intensity was measured with a FACS Aria. Cell fractions stained with both of the labels were detected at positions enclosed by lines (an upper portion in each panel). Since positive cells were observed in two types of CTL lines (0209-01 H2 and 0209-02 D2), it was found that CTL recognizing YLYDRLLRI (SEQ ID NO.: 3) was obtained.

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment(s) of the disclosure. It should be understood that various changes may be made in the function and arrangement of elements without departing from the spirit and scope of the invention as set forth in the appended claims.

Peptide and Polypeptide

The present invention provides a PSF1-derived peptide having CTL inducibility (hereafter, the peptide).

According to the embodiments of the present invention, "PSF1-derived peptide" refers to a peptide fragment consisting of an amino acid sequence which is a part of the amino acid sequence of PSF1 (SEQ ID NO.: 1). The amino acid sequence (SEQ ID NO.: 1) and the nucleic acid sequence (SEQ ID NO.: 2) of PSF1 have been disclosed by GenBank under accession number of NP_066545 and NM_021067, respectively.

The peptide of the present invention was discovered as peptides having high binding affinity to the HLA-A02 antigens. This means that said peptide can form a complex with an HLA-A02 to be presented on the cell surface.

According to the embodiments of the present invention, the phrase "having CTL inducibility" means that the peptide is recognized by a specific CTL. In other word, the peptide has an ability to induce a peptide specific CTL. Although peptides having high binding affinity to the HLA antigens as described above are expected to be highly effective as cancer vaccines, the candidate peptides, which can be available for an active pharmaceutical ingredient, must be examined for the actual presence of CTL inducibility. The ability to induce the peptide specific CTL can be examined by, for example, determining whether or not a cytokine such as interferon-γ (IFN-γ) is produced by peptide-stimulated peripheral blood mononuclear cells (PBMCs) in response to antigen presenting cells which are pulsed with said peptide using the ELISA technique or the like. In addition, cytotoxic activity of the induced CTL can be determined by the $^{51}$Cr-release assay and the like. The peptide of the present invention is preferred to have 8 to 14, more preferably 8 to 11 and especially, 9 or 10 amino acid residues in view of good recognition by CTL.

As a result of examining the CTL inducibility of peptides as described above, it was discovered that peptides having high binding affinity to an HLA antigen did not necessarily have high inducibility. However, peptides selected from peptides comprising the amino acid sequences indicated by YLYDRLLRI (SEQ ID NO.: 3), RALRWEYGSVLPN (SEQ ID NO.: 4) and ALRWEYGSV (SEQ ID NO.: 5) showed particularly high CTL inducibility and cytotoxic activity. These all three peptides are located in the region from 79 to 100 of PSF1 (FIG. 3). With respect to YLYDRLLRI (SEQ ID NO.: 3), peptides including amino acid sequence thereof, AYLYDRLLRI (SEQ ID NO.: 6) or YLYDRLLRIR (SEQ ID NO.: 7), also showed high CTL inducibility. Alternatively, with respect to ALRWEYGSV (SEQ ID NO.: 5), peptides including amino acid sequence thereof, ALRWEYGSVL (SEQ ID NO.: 8) or RALRWEYGSV (SEQ ID NO.: 9), also showed high CTL inducibility.

Embodiments of the present invention also provide peptide derivatives of a PSF1-derived peptide (hereafter, the peptide derivatives). According to the embodiments of the present invention, "a peptide derivative of a PSF1-derived peptide" is a peptide consisting of the amino acid sequence of the PSF1-derived peptide except that substitution, deletion and/or insertion of one or two amino acids have been introduced and having CTL inducibility. Whether or not a peptide derivative has the desired properties can be determined by the above-described procedures.

In order not to alter the property of the original peptide, the substitution of an amino acid is preferably made within the amino acids belonging to the same family, such as polar amino acids, non-polar amino acids, hydrophobic amino acids, hydrophilic amino acids, positively charged amino acids, negatively charged amino acids and aromatic amino acids. The deletion and/or insertion of an amino acid are preferably made so that the number of the amino acid residues consisting of the derivative is 8-14.

In general, peptides that are capable of binding to an Human Leucocyte Antigen (HLA) molecule shares some specific amino acid sequences with regularity depending on the types of the HLA. The specific amino acid sequences with regularity are called as "binding motifs". That is, the binding motif to an HLA-A02 is the sequence wherein the amino acid next to the N-terminal is isoleucine, leucine, valine, methionine, alanine or threonine and that at the C-terminal is isoleucine, leucine, valine, methionine, alanine or threonine (Current Pharmaceutical Design 2010, 16:3149-3157). Binding of a peptide having the HLA-A02 binding motif to an HLA-A02 can be determined using computer analysis such as Bioinformatics and Molecular Analysis Section (NIH, Bethesda, Md.) (Parker K C, et al., J. Immunol. 1994; 152:153-175).

According to the embodiments of the present invention, the substitution, deletion and/or insertion of an amino acid is preferably made so that the derivative is acceptable in view of an HLA binding motif. That is, the substitution, deletion and/or insertion of an amino acid is preferably made so that the amino acid next to the N-terminal is isoleucine, leucine, valine, methionine, alanine or threonine and the C-terminus amino acid is isoleucine, leucine, valine, methionine, alanine or threonine.

The amino acids constituting the peptides and peptide derivatives of the invention may be natural amino acids or amino acid analogues. Amino acid analogues may include N-acylated, O-acylated, esterified, acid amidated and alkylated amino acids. The amino or carboxylic group or the like of the amino acid residue constituting the peptide or peptide derivative of the invention may be modified so long as it does not significantly deteriorate the function of the peptide. The modification may be addition of formyl, acetyl or t-butoxycarbonyl group at the N-terminus- or free-amino group, or addition of methyl, ethyl, t-butyl or benzyl group at the C-terminus- or free carboxylic group. Other modifications may include incorporation of D-amino acids or other amino acid mimetics that can be used, for example, to increase the serum halflife of the peptides.

The peptide and peptide derivative according to the embodiments of the present invention may be synthesized by a conventionally used peptide synthesizing procedure. For example, the peptides can be prepared synthetically, using either recombinant DNA technology or chemical synthesis. Examples of the conventionally used procedures are those described in the literatures including "Peptide Synthesis", Interscience, New York, 1966; "The Proteins", vol. 2, Academic Press Inc., New York, 1976.

Nucleic Acid and a Vector

The present invention further provides a nucleic acid molecule encoding the peptide or peptide derivatives of the invention and a vector comprising said nucleic acid molecule. By introducing the vector comprising the nucleic acid molecule of the invention into an antigen presenting cell, the peptide or peptide derivative of the invention is expressed, and a complex between an HLA and a peptide or peptide derivative of the present invention is presented on the surface of the cell. Thus obtained antigen presenting cell can effectively increase a peptide-specific CTL against tumor cells.

Examples of vectors in which the nucleic acid molecule according to the embodiments of the present invention is incorporated may include various plasmid vectors and viral vectors such as adenovirus, adeno-associated virus, retrovirus and vaccinia virus vectors (Liu M, Acres B, Balloul J M, Bizouarne N, Paul S, Slos P, Squiban P. Gene-based vaccines and immunotherapeutics. Proc. Natl. Acad. Sci. USA 2004; 101 Suppl., 14567-71). Methods for preparing vectors have been well known in the art (Molecular Cloning: A laboratory manual, 2nd ed. New York, Cold Spring Harbor Laboratory).

The vector of the present invention may be administered to a patient so that the peptide or peptide derivative according to the embodiments of the present invention is expressed in antigen presenting cells in the body of the patient. Alternatively, the vector is introduced ex vivo in a suitable cell, for example a dendritic cell derived from the patient, so that the cell expresses the peptide or peptide derivative of the invention, and then the cell is returned to the patient. Those methods are well known in the art (Hrouda D, Dalgleish A G. Gene therapy for prostate cancer. Gene Ther. 1996; 3:845-52).

The amount of the vector to be administered may vary depending on the condition of the disease to be treated, the age and body weight of the patient to be treated and the like, and may preferably be 0.1 μg-100 mg, more preferably 1 μg-50 mg as an amount of DNA. The vector may be administered, for example, intravenously, subcutaneously, or intradermally.

Pharmaceutical Composition

The present invention further provides a pharmaceutical composition for comprising the peptide or peptide derivative according to the embodiment of the present invention, the nucleic acid molecule encoding the said peptide or peptide derivatives, or the vector comprising said nucleic acid molecule. The pharmaceutical composition of the present invention is useful for the treatment or prevention of cancer. Especially, PSF1 is associated with regeneration of the cancer stem cell and so useful for the treatment or the prevention of cancer, which is treatment-resistant to chemotherapy or radiation therapy, recurrent, or metastatic. The pharmaceutical composition of the present invention may comprise one peptide or peptide derivative of the present invention, or a combination of two or more peptides and/or peptide derivatives. Since a cancer patient has a mixture of CTLs recognizing a plurality of different cancer antigen peptides, it is effective to use a plurality of the peptides or peptide derivatives of the present invention in combination. The peptide or peptide derivative of the invention may be used in combination with a cancer antigen peptide other than the peptide of the present invention.

The pharmaceutical composition of the present invention may comprise a pharmaceutically acceptable carrier or the like in addition to the peptide or peptide derivative. Examples of the carrier may include cellulose, amino acid polymers and albumin. The pharmaceutical composition according to the embodiments of the present invention may be formulated as liposomal preparations, particulate preparations in which the ingredient is bound to beads having a diameter of several micrometers, or preparations in which the ingredient is attached to lipids. The pharmaceutical composition of the present invention may be administered along with an adjuvant which has conventionally been used for vaccination in order to establish the immune response effectively. Suitable adjuvants are described in the literature (Johnson A G. Clin. Microbiol. Rev. 1994; 7:277-89). Exemplary adjuvants include, but are not limited to, aluminum phosphate, aluminum hydroxide, and alum. The composition may be administrated intradermally or subcutaneously.

The pharmaceutical composition of the present invention can be used as a cancer vaccine. The dose may be determined based on the condition of the disease to be treated, age and body weight of the respective patient. The amount of the peptide or peptide derivative, according to the embodiments of the present invention, in the pharmaceutical composition may be 0.0001 mg-1000 mg, preferably 0.001 mg-100 mg, more preferably 0.01 mg-10 mg, even more preferably 0.1-5 or 0.5-30 mg. The pharmaceutical composition may preferably be administered, every day, every week, or once every several days, several weeks or several months for 1-3 years.

Method for Inducing CTL

The present invention further provides a method for inducing CTL. According to the embodiments of the present invention, the CTL has cytolytic effect against HLA-A02$^+$ tumor cells. "Cytolytic" refers the property of the CTL which can recognize a complex between a cancer antigen peptide and an HLA on tumor cells and kill the tumor cells. A CTL according to the embodiments of the present invention can be obtained for example by incubating PBMCs collected from an HLA-A02$^+$ cancer patient in vitro in the presence of the peptide or peptide derivative of the present invention. The CTL induced by the present method is useful for the adoptive immunotherapy wherein the induced CTL is returned into the patient from which the PBMCs have been collected to kill cancer cells.

Method for Inducing an Antigen Presenting Cell

Embodiments of the present invention further provide a method for inducing an antigen presenting cell. The method according to the embodiments of the present invention is a method for inducing an antigen presenting cell which can induce a CTL against HLA-A02$^+$ tumor cells. The method may be carried out, for example, by incubating a cell having an antigen-presenting ability derived from a HLA-A02$^+$ cancer patient with the peptide or peptide derivative of the present invention so that the peptide or peptide derivative is bound to an HLA and presented on the cell surface. Alternatively, a vector which encodes the peptide or peptide derivative of the present invention may be introduced into the aforementioned cell such that the peptide or peptide derivative is expressed. The cell having an antigen presenting ability may be, for example, dendritic cell. Dendritic cell derived from a patient can be prepared from PBMCs collected from the patient by separating cells adhered to a culture plate and then incubating the separated cells in the presence of IL-4 and GM-CSF for one week. The antigen presenting cell prepared by the method of the present invention can induce a CTL that specifically recognizes a complex between a peptide or peptide derivative of the present invention and an HLA presented on the surface of the antigen presenting cell. When the antigen presenting cell of the invention is administered to an HLA-A02$^+$ cancer patient, they can induce a tumor-reactive CTL in the body of the patient.

Others

The present invention further provides a method for treating or preventing tumor, which comprises administering the peptide, peptide derivative, or vector according to the embodiments of the present invention to a subject in need thereof. In addition, the present invention also provides use of the peptide, peptide derivative or vector of the present invention for the manufacture of a pharmaceutical composition for the treatment or prevention of tumor.

EXAMPLE

The present invention is further illustrated by the following examples, but is not restricted by these examples in any way.

Example 1: Direct Epitope Discovery

A cellular cytotoxicity T-cell (CTL) derived by a cancer vaccine is considered to recognize a complex of HLA-A02 molecule expressed on the surface of tumor cells and peptide and attack the complex. Thus, proteins, from which peptides are derived, can be cancer antigens. In view of this, a search was conducted for PSF1 sequence peptides capable of binding to HLA-A02 molecules of tumor cells so as to estimate the possibility that PSF1 becomes cancer antigens.
(Method)

A direct epitope discovery method was performed under conditions with reference to a known report (Hawkins et al. J. Proteome. Res. 2008; 7:1445-1457).
Organization of Soluble HLA Vector and Production of Stable Cell Line An expression vector in which a CII tag (collagen type II) sequence was bound to genes coding an extracellular protein region of a human HLA-A02 sequence was organized and introduced to a human mammary carcinoma strain (MDA-MB-231, ATCC), thereby producing a stable cell line.
Purification and Identification of PSF1 Epitope Peptide A conditioned medium of cells or cells obtained by transient forced expression of human PSF1 was collected, and the expressed HLA-A02 molecule was purified with an anti-CII tag antibody column (see International Publication Gazette WO2011/034128). The anti-CII tag antibody column was washed with 150 mM of a NaCl/20 mM Tris buffer and 400 mM of a NaCl/20 mM Tris buffer, and then peptides binding to HLA-A02 molecules were extracted with 10% acetic acid. The extracted peptides were ultrafiltered with an Amicon Ultra 10K (Millipore Co., Temecula, Calif.), and fractionated with an SCX (GL Sciences Inc., Torrence, Calif.). Each fraction was subjected to peptide purification with a C18 column (GL Sciences Inc., Torrence, Calif.) and then to centrifugal concentration with a Speed Vac. A sample subjected to the centrifugal concentration was dissolved in 0.1% TFA/2% acetonitrile again, measured with an LTQ Orbitrap XL (Thermo Fisher Scientific Inc., Carlsbad, Calif.), and then was searched for peptide sequence derived from PSF1 with a MASCOT algorithm (Matrix Science Ltd., London, United Kingdom).
(Results)

Five peptides having the same amino acid sequence (SEQ ID NO: 1) as that of PSF1 were found. Table 1 shows the results. An HLA-A02 molecule peptide complex collected from tumor cells included PSF1 peptides, and thus, the possibility that PSF1 serves as cancer antigens was found. Some identified peptides showed the HLA-A02 binding rule (Nature 1991; 351:290-296), and thus, these peptides were supposed to have CTL inducing activity as cancer vaccine peptides.

TABLE 1

| Initiating amino acid number | Peptide sequence | SEQ ID NO. |
|---|---|---|
| 21 | LPAFNEDGLRQV | 10 |
| 35 | EMKALYEQN | 11 |
| 79 | YLYDRLLRI | 3 |
| 88 | RALRWEYGSVLPN | 4 |
| 130 | GDEGLDITQDMKP | 12 |

Example 2: In Silico Prediction

In Example 1, it was confirmed that PSF1 are cancer antigens, and a plurality of cancer vaccine candidate peptides were identified. On the other hand, in reverse immunology, peptides that can be bonded to HLA-A02 molecules are obtained by using software (Immunology and Cell Biology 2006; 84:318-330). Thus, to obtain PSF1 peptide candidates except those found in Example 1, a software search was carried out.
(Method)

Peptides that can be bonded to HLA-A02 molecules were predicted by using three types of software:
  NetMHC <http://www.cbs.dtu.dk/services/NetMHC>
  BIMAS <http://www-bimas.cit.nih.gov/molbio/hla_bind/>
  SYFPEITHI <http://www.syfpeithi.de/>
To these types of software, a PSF1 full-length amino acid sequence was input, and binding scores regarding peptides of 9 mer and 10 mer were obtained.
(Results)

For peptides of 9 mer and 10 mer derived from full-length PSF1, a plurality of peptides having high scores were obtained. Table 2 shows the scores obtained by using SYFPEITHI (SEQ ID No.: 33). Table 2 suggests the possibility that these peptides bind to HLA-A02 molecules.

TABLE 2

| Initiating amino acid no. | Sequence | SYFPEITHI score | SEQ ID NO. |
|---|---|---|---|
| 5 | KAMELIREL | 25 | 13 |
| 8 | ELIRELHRA | 18 | 14 |
| 31 | QVLEEMKAL | 18 | 15 |
| 35 | EMKALYEQN | 5 | 11 |

TABLE 2-continued

| Initiating amino acid no. | Sequence | SYFPEITHI score | SEQ ID NO. |
|---|---|---|---|
| 69 | LLRNRRCTV | 24 | 16 |
| 79 | YLYDRLLRI | 27 | 3 |
| 89 | ALRWEYGSV | 24 | 17 |
| 120 | SLATYMRSL | 27 | 18 |
| 145 | SLYIEVRCL | 27 | 19 |
| 159 | FEVDDGTSV | 14 | 20 |
| 38 | ALYEQNQDSV | 25 | 21 |
| 68 | SLLRNRRCTV | 26 | 22 |
| 78 | AYLYDRLLRI | 16 | 6 |
| 79 | YLYDRLLRIR | 18 | 7 |
| 88 | RALRWEYGSV | 18 | 9 |
| 89 | ALRWEYGSVL | 22 | 8 |
| 97 | VLPNALRFHM | 15 | 23 |
| 127 | SLGGDEGLDI | 23 | 24 |
| 152 | CLKDYGEFEV | 22 | 25 |
| 176 | FLPRWKCEQL | 21 | 26 |

Example 3: Mouse CTL Induction Assay (ELISPOT Assay)

It was determined whether the PSF1 peptides obtained by Examples above induce peptide specific CTL through HLA-A02.

(Method)

Peptide Immunization and Collection of Responder Cells

The mouse CTL inducing activity with peptides was determined by using mouse immune models. Regarding mice, CB6F1-Tg (HLA-A0201/H2-Kb)A0201 was obtained from Taconic Biosciences, Inc. At most five types of peptide solutions dissolved in DMSO were mixed to produce a PBS solution, and the PBS solution was mixed together with the same amount of MONTANIDE ISA 51VG (SEPPIC), thereby producing an emulsion antigen solution. Then, 50 µL of the antigen solution was used for hypodermic injection into each of two sites at both sides of the belly of the mice (50 µg peptide/mice, N=3-4). Two weeks after the injection, spleen was removed, and spleen cells from which erythrocyte had been eliminated with a solution (BD Pharm Lyse™, Becton, Dickinson and Company, La Jolla, Calif.) were collected as responder cells for an ELISPOT assay.

Production of Stimulator Cells

T2 cells (ATCC) of stimulator cells for use in the ELISPOT assay were produced by incubating, for one night, in an AIM-V culture medium supplemented with immunized assay peptide (30 µg/mL) or negative control peptide (ELAGIGILTV (SEQ ID NO.: 34)).

ELISPOT Assay

The ELISPOT assay was conducted by detecting IFN-γ produced from responder cells. The procedure thereof conformed to an accompanying document of an assay kit, Mouse IFN-γ ELISpot$^{PLUS}$ (MABTECH, Cincinnati, Ohio). Preincubation for the IFN-γ production was performed by adding cells to a 96-well plate included in the assay kit. Stimulator cells were inoculated in a duplicate well or a single well of $5 \times 10^4$ cell/100 µL/well, and then responder cells were added to $2 \times 10^6$ cell/100 µL/well. After one-night coculture, the cells were removed and the well was washed, and then primary antibodies (biotin-antimouse IFN-γ antibodies) included in the assay kit were added. After reaction for two hours at room temperature, the well was washed, supplemented with secondary antibodies (streptavidin-ALP), and subjected to reaction for one hour at room temperature. After having been sufficiently washed, the cells were supplemented with a substrate solution and left for one minute at room temperature. To terminate coloring reaction, the plate was sufficiently washed with running water and was air-dried.

Measurement of the Number of Spots and Measurement Method

The number of blue spots observed at the well bottom was measured with an ImmunoSpot® S5 Verse Analyzer (Cellular Technology Limited, Shaker Heights, Ohio). Measurement values of unclear spots because of a wide range of coloring were not used. An average value was obtained for the duplicate well, and the difference from the negative control was calculated in order to obtain the number of spots specific to peptides. The average value and the SD value were calculated by using values for individual mice, and the case having a positive number of differences between the average value and the SD value was determined as positive.

(Results)

Peptide specific spots were observed in peptides shown in Table 3, and 10 of these peptides were determined to be positive. Since specific CTL were induced by PSF1 derived peptides, it was confirmed that peptides were presented by HLA-A02, and mouse CTL recognizing PSF1 derived peptides was induced. Although the results were obtained for a mouse immune system, the reaction occurs through HLA-A02, which is human MHC, and thus, it was suggested that there is the possibility of similar induction of CTL in humans.

TABLE 3

| Initiating amino acid number/ SEQ ID NO. | Sequence | Specific spot number (Ave ± SD) | Initiating amino acid number/ SEQ ID NO. | Sequence | Specific spot number (Ave ± SD) |
|---|---|---|---|---|---|
| 9 mer | | | 10 mer | | |
| 5/13 | KAMELIREL | 22 ± 13 | 38/21 | ALYEQNQDSV | 30 ± 15 |
| 31/15 | QVLEEMKAL | 7 ± 7 | 68/22 | SLLRNRRCTV | 1 ± 2 |

TABLE 3-continued

| Initiating amino acid number/ SEQ ID NO. | Sequence | Specific spot number (Ave ± SD) | Initiating amino acid number/ SEQ ID NO. | Sequence | Specific spot number (Ave ± SD) |
|---|---|---|---|---|---|
| 35/11 | EMKALYEQN | 6 ± 8 | 78/6 | AYLYDRLLRI | 23 ± 21 |
| 69/27 | LIRNRRCTV | 7 ± 9 | 79/7 | YLYDRLLRIR | 165 ± 17 |
| 79/3 | YLYDRLLRI | 80 ± 18 | 97/23 | VLPNALRFHM | 127 ± 41 |
| 120/18 | SLATYMRSL | 70 ± 79 | 152/25 | CLKDYGEFEV | 53 ± 28 |
| 145/19 | SLYIEVRCL | 43 ± 24 | 176/26 | FLPRWKCEQL | 31 ± 24 |
|  |  |  | 21/10 | LPAFNEDGLRQV | 3 ± 8 |
|  |  |  | 88/28 | RALRWEYGSVLPN | 29 ± 22 |
|  |  |  | 130/12 | GDEGLDITQDMKP | 1 ± 2 |

Example 4: Human CTL Induction Assay (ELISPOT Assay)

It was determined whether the PSF1 peptides obtained in Examples 1 and 2 induce peptide specific human CTL.
(Method)
A human CTL induction assay was conducted under conditions with reference to a known report (Harano et al. Int. J. Cancer 2008; 123:2616-2625).
Collection of Peripheral Blood Mononuclear Cells Heparinized peripheral blood of healthy volunteers having HLA-A0201 was subjected to centrifugation at 3000 rpm for 20 minutes, thereby removing plasma. Cell pellets were supplemented with HBSS(−) (Wako Pure Chemical Industries, Ltd, Richmond, Va.) to which 5 mM of HEPES (SIGMA, Carlsbad, Calif.) had been added, and were suspended, thereby overlaying the suspension over a Ficoll-paque PREMIUM (GE Healthcare, Ltd., Pittsburgh, Pa.). Then, 400 g of the resulting substance was subjected to centrifugation for 40 minutes, and peripheral blood monocyte cells (PBMCs) separated as an intermediate layer were collected.
Preparation of CD14-Positive Cells and CD8-Positive Cells PBMCs were supplemented with CD14 microbeads (Miltenyi Biotec K.K.), and caused to react at 4° C. for 15 minutes. The cells were passed through LS columns (Miltenyi Biotec K.K., Tokyo, Japan), and CD14-positive cells were obtained by using QuadroMACS™ Separator (Miltenyi Biotec K.K., Tokyo, Japan). The rest of the cells were collected and washed, and then supplemented with CD8 microbeads (Miltenyi Biotec K.K., Tokyo, Japan) and allowed to react at 4° C. for 15 minutes. Thereafter, a similar process is performed, thereby obtaining CD8-positive cells. The CD14-positive cells were subjected to differentiation induction to monocyte-derived dendritic cells (Mo-DCs), and CD8-positive cells were temporarily frozen for storage.
Differentiation Induction to Mo-DC and Production of Peptide-Presenting Cells Since CD8-positive cells were subjected to antigen stimulation twice, peptide-presenting cells were produced twice accordingly. CD14-positive cells were disseminated in two RepCell plates (CellSeed Inc., Tokyo, Japan), and incubated in a 5% $CO_2$ incubator at 37° C. with a culture solution in which 100 ng/ml GM-CSF (R&D Systems, Minneapolis, Minn.) and 10 ng/ml IL-4 (R&D Systems) were added to an AIM-V (Invitrogen Corporation, Carlsbad, Calif.) culture medium including antibiotic and serum.

First production of peptide-presenting cells was started 5-7 days after the start of incubation. To one of the plates, 0.1 KE/ml OK-432 (Chugai Pharmaceutical Co., Ltd., Tokyo, Japan) was added, and on the next day, cells were collected and inoculated in a 96-well U-bottom plate. Then, 20 μg/ml of assay peptide of one type was added to each half area (48 wells) of the plate, and incubated for one day at 37° C. in a 5% $CO_2$ incubator, thereby producing peptide-presenting cells. Second production was performed similarly on the other plate 12-14 days after the start of incubation.

CTL Induction by Antigen Stimulation Using Peptide-Presenting Cells and Preparation of Responder Cells Peptide-presenting cells in a 96-well plate were irradiated with X rays (30 Gy), and the frozen stored CD8-positive cells were added to all the wells, thereby performing first antigen stimulation. As a culture solution, a solution in which 10 ng/ml IL-7 (R&D Systems, Minneapolis, Minn.) was added to an AIM-V culture medium including antibiotic and serum was used. After incubation for seven days, cells included in supernatant were collected and cocultured with peptide-presenting cells (after X-ray irradiation) obtained by the second production, thereby performing second antigen stimulation in the 96-well plate. At this time, 20 U/mL of IL-2 (Shionogi & Co., Ltd., Florham Park, N.J.) was added to the culture solution. After further incubation for seven days, cells in supernatant including CTL were collected and washed with an AIM-V culture medium including antibiotic and serum to have a concentration of approximately $2 \times 10^5$ cells/ml per well, thereby obtaining responder cells for an ELISPOT assay.

Production of Stimulator Cells

T2 cells of stimulator cells for use in an ELISPOT assay were produced by incubating the cells for one night in an AIM-V culture medium supplemented with an assay peptide (20 μg/mL). As stimulator cells of a negative control, only T2 cells were used (without peptides). The cells were irradiated with X rays (30 Gy) and washed with an AIM-V culture medium including antibiotic and serum to have a concentration of $2 \times 10^5$ cells/ml.

ELISPOT Assay

An ELISPOT assay was conducted by detecting IFN-γ produced from responder cells. The procedure thereof conformed to an accompanying document of an assay kit, ELISpotPRO for Human IFN-γ (MABTECH, Cincinnati, Ohio). Responder cells in an amount of 100 μL/well were added for each 2 wells to a 96-well plate of the assay kit, and 100 μL/well of stimulator cells supplemented with assay peptides or stimulator cells (without peptides) of a negative control were inoculated in each well. After incubation for one night, the wells were washed so that the cells were removed from the wells, and ALP-labeling anti-IFN-γ antibodies included in the assay kit were added. After reaction at room temperature for two hours, the cells were sufficiently washed, supplemented with a substrate solution, and left at room temperature for five minutes. To terminate coloring reaction, the plate was sufficiently washed with running water and was air-dried.

Measurement of the Number of Spots and Measurement Method

The number of blue spots observed at the well bottom was measured with an ImmunoSpot® S5 Verse Analyzer. In a well including the same responder cells, the number of peptide specific spots was calculated by subtracting the number of spots caused by stimulator cells (without peptides) of a negative control from the number of spots caused by peptide-added stimulator cells. Assuming that cells showing a difference of 50 or more were defined to be positive, the following seven peptides were determined to be positive in the examination on a plurality of donors.

(Results)

Human CTL in which seven peptides shown in Table 4 below were specific was induced. Since specific CTL was induced by PSF1-derived peptides, it was found that CTL recognizing PSF1 derived peptides exist in humans. This suggests the possibility that these PSF1 peptides can be a cancer vaccine.

ELISPOT Assay Results

TABLE 4

| Initiating peptide number | Sequence | Positive donor number | SEQ ID NO. | Donor number | Donor positive percentage |
|---|---|---|---|---|---|
| 21 | LPAFNEDGLRQV | 0 | 29 | 7 | 0% |
| 35 | EMKALYEQN | 1 | 11 | 8 | 13% |
| 79 | YLYDRLLRI | 6 | 3 | 13 | 46% |
| 145 | SLYIEVRCL | 2 | 30 | 2 | 100% |
| 88 | RALRWEYGSVLPN | 1 | 4 | 8 | 13% |
| 88 | RALRWEYGSV | 3 | 9 | 5 | 60% |
| 89 | ALRWEYGSVL | 2 | 8 | 2 | 100% |
| 89 | ALRWEYGSV | 2 | 17 | 5 | 40% |
| 130 | GDEGLDITQDMKP | 0 | 12 | 7 | 0% |

Example 5: Human CTL Induction Assay (Tetramer Assay)

To confirm induction of PSF1 peptide specific CTL with another method, a Tetramer assay was conducted.

(Method)

Production of CTL Line

Cells that had been determined to be positive in the above-described ELISPOT assay was continued to be incubated with a culture solution in which 100 ng/ml of IL-15 (Miltenyi Biotec K.K., San Diego, Calif.) was added to an AIM-V culture medium including antibiotic and serum.

Tetramer Assay

Tetramer (Medical & Biological Laboratories Co., Ltd: MBL) for PSF1 peptides (YLYDRLLR, SEQ ID NO.: 31) was produced. Cells of a CTL line were collected, colored with tetramer and APC H7 marker anti-CD8 antibodies (SK-1) (Becton, Dickinson and Company, La Jolla, Calif.), and measured with a FACS Aria (Becton, Dickinson and CompanyLa Jolla, Calif.). Two types of CTL lines (0209-01 H2 and 0209-02 D2) were used.

(Results)

As shown in FIG. 1, since a cell population that reacts with both anti-CD8 antibodies and tetramer was observed in each CTL line, it was found that CTL lines recognizing PSF1 peptides were produced. Observation of Tetramer-positive cells directly proved the presence of peptide-specific human CTL.

Example 6: Human CTL Cytotoxic Assay

To examine whether a CTL line has an activity of attacking cells, a cytotoxic assay was conducted.

Specifically, assay conditions were set with reference to a method described in a known report (New CFSE-based assay to determine susceptibility to lysis by cytotoxic T cells of leukemic precursor cells within a heterogeneous target cell population. Jedema I. et al. Blood 2004; 103:2677-2682).

Production of Target Cells

As target cells for use in the cytotoxic assay, 1 μM of CellTracker™ Green CMFDA (5-chloromethylfluorescein diacetate) (Invitrogen Corp., Carlsbad, Calif.) was added to T2 cells, and these cells were allowed to react with each other at 37° C. for 15 minutes. The T2 cells were labeled with CMFDA, which is a fluorescent marker, washed with AIM-V, supplemented with assay peptides (20 μg/ml), and incubated for one night. As target cells of a negative control, T2 cells only labeled with a fluorescent marker were used (without peptide addition). The cells were washed with an AIM-V culture medium including antibiotic and serum to have a concentration of $5 \times 10^4$ cells/ml.

Production of Effector Cells

For effector cells for use in the cytotoxic assay, three types of CTL lines (0209-1 H2; YLYDRLLRI (SEQ ID NO.: 3), 1004-1 P-13-1_2; RALRWEYGSVLPN (SEQ ID NO.: 4), and 1004-1 P-10-9_1; ALRWEYGSVL (SEQ ID NO.: 32)) obtained by incubation after the above-described ELISPOT assay were used. The cells were prepared to have concentrations of 50, 15, $5 \times 10^4$ cells/ml after washing with AIM-V. The preparation was performed with an AIM-V culture medium including antibiotic and serum.

Cytotoxic Assay

Target cells (T) supplemented with peptides used in CTL induction or target cells (T) of a negative control supplemented with no peptides were mixed with effector cells (E) at a cell ratio (E/T ratio) of 10:1, 3:1, and 1:1, and cocultured for one night. Immediately before measurement with a MACS Quant (Miltenyi Biotec, San Diego, Calif.) or a FACS Aria, 0.1 μg/ml of DAPI was added in order to distinguish living cells from dead cells by means of staining. In an analysis, the proportion of DAPI-negative cells (living cells) in target cells labeled with CMFDA was obtained, and the survival rate of target cells was calculated using incubation conditions (only for target cells) where coculture with effector cells was not performed as 100%.

(Results)

Figures 2, 2C:
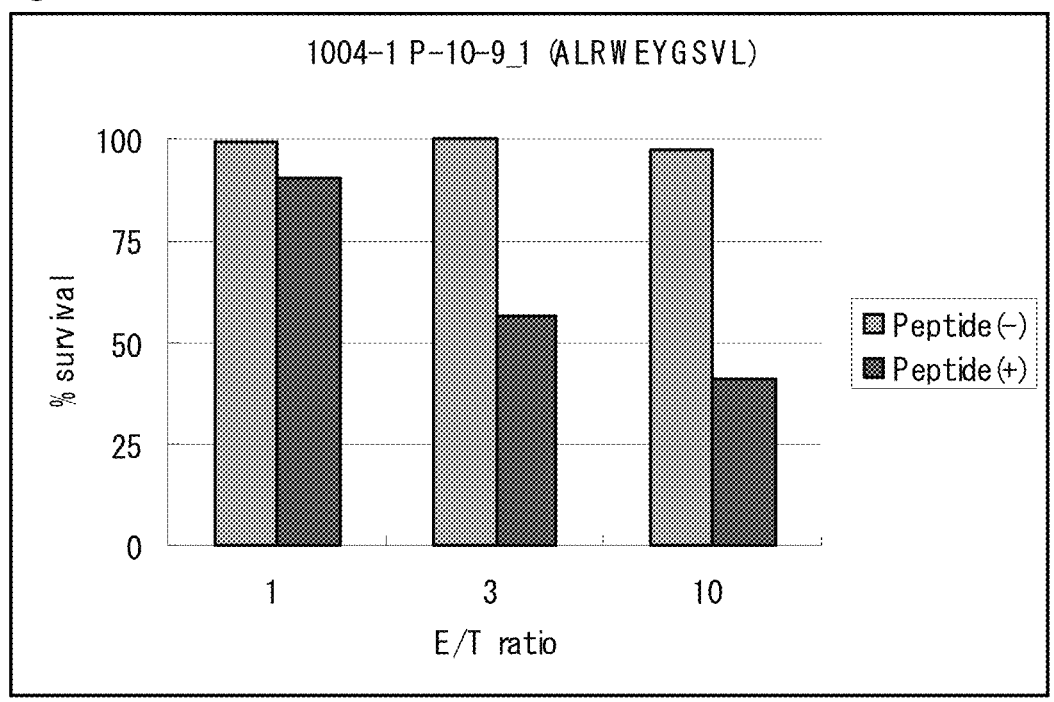
FIG. 2C shows cellular cytotoxicity by a peptide specific CTL line. Peptide-pulsed cells (peptide+) or peptide-non-pulsed cells (peptide-) obtained from CTL specific to peptide ALRWEYGSVL (SEQ ID NO.: 8) (E; effector cell) and T2 cells (T; target cell) were cocultured at an E:T cell ratio of 1:1, 3:1, and 10:1. On the next day, the survival rate of target cells was obtained. Then, it was found that the survival rate of target cells pulsed with peptides decreased to a degree greater than target cells not pulsed with peptides. In addition, since the survival rate decreased in accordance with the ratio of cocultured cells, cellular cytotoxicity by peptide specific CTL was demonstrated.

As shown in FIG. 2, in the assay on each of the CTL lines, the survival rate of target cells supplemented with peptides was lower than that of target cells of a negative control (without peptides). It was found that the three types of CTL lines induced by peptides showed specific recognition of peptides and show cytotoxic effect. This suggests the possibility that tumor cells presenting PSF1 peptides on the cell surfaces are damaged by CTL recognizing PSF1 peptides, and thus, suggests that PSF1 peptides can be a cancer vaccine.

The present invention provides a peptide inducing CTL significantly, a DNA encoding of said peptide, a pharmaceutical composition comprising said peptide and said DNA, and a cancer vaccine using said peptide and said DNA.

While the principles of the disclosure have been described above in connection with specific examples, it is to be clearly understood that this description is made only by way of example and not as limitation on the scope of the invention.

The invention claimed is:

1. A method of inducing cytotoxic T-cell activity in a cell comprising the steps of:
    administering a peptide selected from the group consisting of the amino acid sequences of SEQ ID NO: 3, SEQ ID NO: 4, SEQ ID NO: 5, SEQ ID NO: 6, SEQ ID NO: 7, SEQ ID NO: 8, SEQ ID NO: 9, wherein at least one of the amino acids of said amino acid sequence optionally consists of N-terminal acylation or C-terminal amidation, and the peptide has cytotoxic T-cell inducibility to the cell.

2. The method according to claim 1, wherein the said amino acid sequence includes a formyl group, an acetyl group, or a t-butoxycarbonyl group at the N-terminus of the peptide.

3. The method according to claim 1, wherein the said amino acid sequence includes a methyl group, an ethyl group, a t-butyl or a benzyl group on the C-terminus of the peptide.

4. The method according to claim 1, wherein the cell is an antigen presenting cell.

5. The method according to claim 4, wherein the antigen presenting cell is obtained from a Human leucocyte Antigen-A02 (HLA-A-A02) positive (HLA-A02$^+$) cancer patient.

6. The method according to claim 5, wherein a cancer cell obtained from the cancer patient expresses Partner of Sld five 1 (PSF 1) on its surface.

* * * * *